United States Patent
Ferree

(12) 
(10) Patent No.: US 6,352,557 B1
(45) Date of Patent: Mar. 5, 2002

(54) TREATING DEGENERATIVE DISC DISEASE THROUGH TRANSPLANTION OF EXTRACELLULAR NUCLEUS PULPOSUS MATRIX AND AUTOGRAFT NUCLEUS PULPOSUS CELLS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 8 days.

(21) Appl. No.: 09/638,727

(22) Filed: Aug. 14, 2000

Related U.S. Application Data

(60) Provisional application No. 60/148,913, filed on Aug. 13, 1999.

(51) Int. Cl.$^7$ .................................................. A61F 2/44
(52) U.S. Cl. ................... 623/17.11; 623/17.16; 424/93.7
(58) Field of Search .................... 623/17.11–17.16, 623/919, 908; 424/93.7

(56) References Cited

U.S. PATENT DOCUMENTS

| | | | | |
|---|---|---|---|---|
| 5,514,180 A | * | 5/1996 | Heggeness et al. ...... | 623/17.11 |
| 5,545,229 A | * | 8/1996 | Parsons et al. ......... | 623/17.11 |
| 6,060,053 A | * | 5/2000 | Atala ..................... | 424/93.7 |
| 6,077,987 A | * | 6/2000 | Breitbart et al. ........ | 623/11.11 |
| 6,183,518 B1 | * | 2/2001 | Ross et al. .............. | 623/17.16 |
| 6,187,048 B1 | * | 2/2001 | Milner et al. ............ | 623/17.12 |
| 6,231,615 B1 | * | 5/2001 | Preissman ............... | 623/17.11 |

OTHER PUBLICATIONS

Steven Frick MD, Lumbar Intervertebral Disc Transfer, "Spine", vol. 19, No. 16 pp. 1826–1835.*
"Proceedings 13th Annual Meeting" North American Spine Society, Oct. 1998.
Orthopedics Today, Jul. 2000.
"Proceedings 14th Annual Meeting" North American Spine Society, Oct. 1999.

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Living nucleus pulposus cells are combined with nucleus pulposus extracellular matrix obtained from recently deceased human or animal donors to restore disc function and eliminate pain in patients with disc disease. In the preferred embodiment, the engineered nucleus is morselized to allow insertion through a small puncture in the annulus fibrosis with a needle and syringe. Additional therapeutic substances like culture medium, growth factors, differentiation factors, hydrogels polymers, antibiotics, anti-inflammatory medications, or immunosuppressive medications could be added to the transplanted nucleus pulposus tissue.

23 Claims, No Drawings

TREATING DEGENERATIVE DISC DISEASE THROUGH TRANSPLANTION OF EXTRACELLULAR NUCLEUS PULPOSUS MATRIX AND AUTOGRAFT NUCLEUS PULPOSUS CELLS

REFERENCE TO RELATED APPLICATIONS

This application claims priority of U.S. provisional patent application Serial No. 60/148,913, filed Aug. 13, 1999, the entire contents of which are incorporated herein by reference.

FIELD OF THE INVENTION

This invention relates generally to the treatment of diseased or traumatized intervertebral discs, and more particularly, to the use of engineered disc tissues in conjunction with such treatment.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncollagenous proteins.

The cells of the nucleus pulposus have chondrocyte-like features. Blood vessels do not course into the nucleus pulposus. Rather, the cells of the nucleus pulposus of the adult human obtain nutrients and eliminate waste by diffusion through blood vessels in the end plates of the vertebrae adjacent to the disc.

The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. The future of treating degenerative disc disease therefore lies in treatments which preserve disc function. If disc function could be restored with biologic replacement or augmentation, the risk of premature wear out would be minimized, if not eliminated.

SUMMARY OF THE INVENTION

Although transplantation of living cells risks rejection by graft host reaction, this invention broadly recognizes that transplantation of the extracellular matrix of the nucleus pulposus is unlikely to incite a graft host reaction. In the preferred embodiment, autograft nucleus pulposus cells are harvested, cultured, then added to nucleus pulposus extracellular matrix obtained from recently deceased humans or animals. The combined nucleus pulposus material is then introduced into the injured or diseased disc.

The cells or engineered tissues may be introduced using any surgical technique, including percutaneous or laparoscopic approaches. As one delivery mechanism, a passageway may be formed through the annulus fibrosis, with the cells or engineered disc tissue being introduced into the disc through the passageway. In particular, the engineered disc tissue may be morselized and injected into the disc with a needle and syringe or through a small cannula.

The method of the invention may further include the step of adding one or more therapeutic substances to the cells prior to transplantation. Such therapeutic substances could include culture media, growth factors, differentiation factors, hydrogels, polymers, antibiotics, anti-inflammatory medications, immunosuppressive medications, or any useful combination thereof.

DETAILED DESCRIPTION OF THE INVENTION

Broadly according to the method of this invention, autograft nucleus pulposus cells are harvested, cultured, added to nucleus pulposus extracellular matrix material, then injected into the injured or diseased disc. The nucleus pulposus cells and extracellular matrix are preferably harvested from a live human, though recently deceased human or animal donors may alternatively be used. Depending upon the extent of the harvest, the recipient may function at least in part as a donor, or the tissues from others, including fetal sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described.

Following nucleus pulposus harvest, the tissue is processed to kill the living cells. Care is taken to preserve the extracellular matrix. Guidelines for processing the harvested nucleus pulposis as described are well known to those skilled in the art. For example, the tissue could be frozen and thawed.

Autologous nucleus pulposus chondrocyte like cells are obtained by aspiration or biopsy of healthy discs of the patient. The harvested nucleus pulposus cells are isolated and cultured using standard techniques. The harvested sterile nucleus pulposus is morselized and washed with phosphate buffered saline. The cells are released from the extracellular matrix with 0.2% clostridial collagenase (Worthington CLS II, 140u/mg) and agitated. See Klagsburn, "Methods in Enzvmology, Vol. VII. The resulting suspension is filtered with a 153.mu.g nylon sieve (Tetko, Elmford, N.Y.).

The filtered solution is then centrifuged at 1800 rpm to remove the cells. The supernatant above the cells is removed with a micropipette until the cell concentration reaches $5.\text{times}.10.\text{sup}.7$ cells/cc. The harvested cells are grown in Hamm's F-12 culture media, 10% fetal calf serum, L-glutamine (292.mu.g/cc), penicillin (100u/cc), streptomycin (100.mu.g/cc), and ascorbic acid (5.mu.g/cc) at 37.degrees C. The above method is described in detail in U.S. Pat. No. 6,060,053, which is incorporated in its entirety herein by reference.

Precursor cells of nucleus pulposus cells, chondrocytes, or other living cells that could function like nucleus pulposus cells or that could differentiate into cells to build a functional nucleus pulposus may also be used.

The living cells from cell culture are implanted into the donor extracellular matrix to form a living nucleus pulposus.

In the preferred embodiment, the donor extracellular matrix is morselized. Morselization of the extracellular matrix increases the surface area for cell attachment, aides diffusion after implantation, and allows the introduction of the transplanted nucleus tissue into the degenerated or diseased disc through a needle or small cannula. Alternatively, small holes could be drilled into the donor extracellular matrix for cell attachment.

The living cells and extracellular matrix may be injected into the patient immediately after combination or after a period of time to allow attachment of the cells to the matrix. Naturally, in the delayed injection embodiment, the cells would be supported with tissue culture media.

The collagen fibers of the annulus fibrosis are arranged in 15–25 layers or lamella. The fibers of the lamella alternate direction between layers. A blunt tipped needle or cannula could be forced through the annulus. Upon withdraw of the needle, after injecting the transplanted nucleus pulposus, the separated fibers of the lamella would return to their normal position, sealing the annulus. The annulus fibrosis is thicker in the anterior and lateral portion of the disc. Thus, in the preferred embodiment, the needle would be inserted into the anterior or lateral portion of the disc. Those skilled in the art will realize the needle could be directed into the lateral portion of the disc percutaneously with fluourscopic guidance and into the anterior portion of the disc laparoscopically.

In the preferred embodiment, the transplanted nucleus is added to the patient's nucleus pulposus. Alternatively, the patient's nucleus could be removed with standard techniques (enzymatically (chymopapain) or with the aid of a laser, suction device, shaver, or other surgical instrument). If the nucleus is removed the hole in the annulus must be small and closed at the end of the procedure.

Additional therapeutic substances could be added to the transplanted nucleus. For example, resorbable culture medium, tissue growth or differentiation factors (recombinant generated morphogenetic proteins, PDGF, TGF-$\beta$, EGF/TGF-$\alpha$, IGF-I, $\beta$FGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be beneficial.

I claim:

1. A method of treating a diseased or traumatized intervertebral disc having a nucleus and annulus fibrosis, comprising the steps of:
   harvesting nucleus pulposus cells from a healthy intervertebral disc;
   harvesting the extracellular matrix of the nucleus pulposus from a recently deceased human or animal;
   combining the harvested cells with the harvested extracellular matrix to produce an engineered nucleus pulposus; and
   transplanting the engineered nucleus pulposus into the disc.

2. The method of claim 1, further including the steps of:
   morselizing the engineered nucleus pulposus;
   forming a passageway through the annulus fibrosis; and
   transplanting the engineered nucleus pulposus into the disc through the passageway.

3. The method of claim 1, further including the step of adding one or more therapeutic substances to the engineered nucleus pulposus.

4. The method of claim 3, wherein the therapeutic substances include one or more of the following:
   culture media, growth factors, differentiation factors, hydrogels, polymers, antibiotics, anti-inflammatory medications, or immunosuppressive medications.

5. The method of claim 1, wherein the step of transplanting the engineered nucleus pulposus into the disc includes injecting the engineered disc tissue into the disc through a needle and syringe or small cannula.

6. The method of claim 1, wherein the step of transplanting the engineered nucleus pulposus includes percutaneously or laparoscopically injecting the engineered disc tissue into the disc being treated.

7. The method of claim 1, further including the step of keeping the harvested cells viable until placed into the disc being treated.

8. A method of treating a diseased or traumatized intervertebral disc having a nucleus and annulus fibrosis, comprising the steps of:
   harvesting cells that differentiate into nucleus pulposus like cells, or live cells that function like cells of the nucleus pulposus;
   harvesting the extracellular matrix of the nucleus pulposus from a recently deceased human or animal;
   combining the harvested cells with the harvested extracellular matrix to produce an engineered nucleus pulposus; and
   transplanting the engineered nucleus pulposus into the disc.

9. The method of claim 8, further including the steps of:
   morselizing the engineered nucleus pulposus;
   forming a passageway through the annulus fibrosis; and
   transplanting the engineered nucleus pulposus into the disc through the passageway.

10. The method of claim 8, further including the step of adding one or more therapeutic substances to the engineered nucleus pulposus.

11. The method of claim 10, wherein the therapeutic substances include one or more of the following:
   culture media, growth factors, differentiation factors, hydrogels, polymers, antibiotics, anti-inflammatory medications, or immunosuppressive medications.

12. The method of claim 8, wherein the step of transplanting the engineered nucleus pulposus into the disc includes injecting the engineered disc tissue into the disc through a needle and syringe or small cannula.

13. The method of claim 8, wherein the step of transplanting the engineered nucleus pulposus includes percutaneously or laparoscopically injecting the engineered disc tissue into the disc being treated.

14. The method of claim 8, further including the step of keeping the harvested cells viable until placed into the disc being treated.

15. A method of preparing an engineered nucleus pulposus, comprising the steps of:
   harvesting nucleus pulposus cells from a healthy intervertebral disc;
   harvesting the extracellular matrix of the nucleus pulposus from a recently deceased human or animal;
   combining the harvested cells with the harvested extracellular matrix to produce an engineered nucleus pulposus; and
   keeping the engineered nucleus pulposus viable until transplantation.

16. An engineered nucleus pulposus according to the method of claim 15.

17. The engineered nucleus pulposus of claim 16, wherein the constituents are morselized.

18. The engineered nucleus pulposus of claim 16, further including one or more therapeutic substances.

19. The engineered nucleus pulposus of claim 18, wherein the therapeutic substances include one or more of the following:

culture media, growth factors, differentiation factors, hydrogels, polymers, antibiotics, anti-inflammatory medications, or immunosuppressive medications.

20. A method of preparing an engineered nucleus pulposus, comprising the steps of:

harvesting cells that differentiate into nucleus pulposus like cells, or live cells that function like cells of the nucleus pulposus;

harvesting the extracellular matrix of the nucleus pulposus from a recently deceased human or animal;

combining the harvested cells with the harvested extracellular matrix to produce an engineered nucleus pulposus; and keeping the engineered nucleus pulposus viable until use.

21. The engineered nucleus pulposus of claim 20, wherein the constituents are morselized.

22. The engineered nucleus pulposus of claim 20, further including one or more therapeutic substances.

23. The engineered nucleus pulposus of claim 22, wherein the therapeutic substances include one or more of the following:

culture media, growth factors, differentiation factors, hydrogels, polymers, antibiotics, anti-inflammatory medications, or immunosuppressive medications.

* * * * *